United States Patent [19]
Bankert et al.

[11] Patent Number: 5,266,271
[45] Date of Patent: Nov. 30, 1993

[54] MICROSENSOR COPOLYMER AND METHOD OF MANUFACTURE

[75] Inventors: Charles S. Bankert, Oceanside; Henry K. Hui, Laguna Niguel; Alan M. Nelson, San Diego, all of Calif.

[73] Assignee: Puritan-Bennett Corporation, Carlsbad, Calif.

[21] Appl. No.: 887,476

[22] Filed: May 22, 1992

[51] Int. Cl.$^5$ .................................. G01N 21/64
[52] U.S. Cl. ........................ 422/82.07; 8/552; 8/647; 8/648; 385/12; 422/82.06; 422/82.08; 422/82.11
[58] Field of Search ............... 422/82.06–82.08, 422/82.11, 57–58; 385/12; 8/552, 647, 648

[56] References Cited

U.S. PATENT DOCUMENTS

| | | |
|---|---|---|
| 3,668,189 | 6/1972 | Goetz . |
| 3,904,373 | 9/1975 | Harper . |
| 4,194,877 | 3/1980 | Peterson ........................ 8/4 |
| 4,200,110 | 4/1980 | Peterson et al. ............. 422/58 X |
| 4,468,229 | 8/1984 | Su ............................... 8/507 |
| 4,560,248 | 12/1985 | Cramp et al. .............. 128/634 X |
| 4,712,865 | 12/1987 | Hsu et al. .................. 128/634 X |
| 4,714,770 | 12/1987 | Hsu et al. .................. 556/419 |
| 4,746,751 | 5/1988 | Oviatt, Jr. et al. ........... 556/456 |
| 4,798,738 | 1/1989 | Yafuso et al. ............... 427/2 |
| 4,803,049 | 2/1989 | Hirschfeld et al. ......... 422/82.07 X |
| 4,868,251 | 9/1989 | Reich et al. ................ 525/479 |
| 4,886,338 | 12/1989 | Yafuso et al. .............. 128/634 X |
| 4,906,249 | 3/1990 | Fogt et al. ................. 128/634 X |
| 4,921,589 | 5/1990 | Yates et al. ................ 204/157.5 |
| 4,925,268 | 5/1990 | Iyer et al. . |

FOREIGN PATENT DOCUMENTS

| | | |
|---|---|---|
| 0283206A2 | 9/1988 | European Pat. Off. . |
| 0313655 | 5/1989 | European Pat. Off. . |
| 0336986A1 | 10/1989 | European Pat. Off. . |
| 3343636A1 | 12/1983 | Fed. Rep. of Germany . |
| WO88/05533 | 7/1988 | PCT Int'l Appl. . |

OTHER PUBLICATIONS

Munkholm and Walt, *Polymer Modification of Fiber Optic Chemical Sensors as a Method of Enhancing Fluorescence Signal for pH Measurement*, pp. 1427–1430, Anal. Chem., 1986.

Jordan and Walt, *Physiological pH Fiber-Optic Chemical Sensor Based on Energy Transfer*, pp. 437–439, Anal. Chem. 1987.

Munkholm and Walt, *A Fiber-Optic Sensor For $CO_2$ Measurement*, pp. 109–112, vol. 35, 1988.

*Primary Examiner*—Jill A. Johnston
*Attorney, Agent, or Firm*—Fulwider, Patton, Lee & Utecht

[57] ABSTRACT

The optical fiber microsensor includes an optical fiber having a portion of the surface of a light conducting core covered with a layer containing an analyte sensitive dye material. The dye indicator material is covalently bonded to a copolymer which is covalently bonded to a blocked polyether polyisocyanate. The resulting polymer is covalently bonded to the optical fiber core to prevent leaching of the indicator dye material during extended use.

23 Claims, 1 Drawing Sheet

MICROSENSOR COPOLYMER AND METHOD OF MANUFACTURE

BACKGROUND OF THE INVENTION

1. Field of the Invention

This invention is generally directed to chemical and biochemical quantitative analysis, and more specifically concerns an optical fiber sensor for measuring multiple parameters such as oxygen, carbon dioxide, and pH of a fluid or gaseous mixture.

2. Description of Related Art

Fiber-optic based devices for measuring concentrations of pH, oxygen and carbon dioxide have found numerous applications in the medical, chemical and environmental fields. Optical fiber sensors have also now been developed for taking in vivo, intravascular measurements of blood analytes, such as pH, oxygen and carbon dioxide. Many such sensors rely on the phenomenon of dye fluorescence in response exposure to an excitation wavelength of light as a means for measuring the presence of analyte in a liquid or gaseous mixture. Fluorescence dye indicators have been widely used for such devices due to the high sensitivity that can be achieved. Systems and instruments implementing fluorescence techniques typically utilize an encapsulated fluorescent dye whose fluorescence emissions are affected by the presence of the analyte of interest. The fluorescent dye can be placed within a semi-permeable matrix made from a polymer or similar substance. A light source with appropriate filtering system provides a selected wavelength of light which propagates down the optical fiber and excites the dye. The fluorescence signal, induced by the excitation energy, can also return via the same optical fiber, to be measured by a photodetector. The intensity of the fluorescence of the dye, which is a function of the analyte level in the sample, can be transduced into a measure of the concentration of the analyte of interest.

A fluorescent sensor typically utilizes light in one wavelength region to excite the fluorescent indicator dye to emit light of a different wavelength. Such a sensor may for example utilize a single dye that exists in an acid form and a base form, each with a different excitation wavelength to measure pH.

The concentration of carbon dioxide in a solution can be determined by an optical sensor by measuring the pH of a solution of bicarbonate in equilibrium with the carbon dioxide in the solution. The bicarbonate and carbon dioxide form a pH buffer system in which the hydrogen ion concentration generally varies with the carbon dioxide concentration. The pH or carbon dioxide content of a solution may, for example, be measured with a fiber optic sensor utilizing fluorescein as a fluorescence indicator enclosed in a silicone matrix at the end of an optical fiber. Another type of fluorescence indicator which has been used is hydroxypyrenetrisulfonic acid (HPTS).

Techniques implementing fluorescence quenching for measuring the partial pressure of oxygen have been developed which utilize an encapsulated oxygen-quenchable fluorescence dye that is placed within a gas permeable matrix usually made from a polymer or similar substance. The intensity of the fluorescence of the dye, which is a function of the oxygen level in the sample, can be transduced into a partial pressure of oxygen.

Relatively bulky multiple optical fiber sensor probes having separate optical fiber sensing elements for each analyte have been developed, but are complex and difficult to manufacture. Although an optical fiber fluorescent dye based sensor for sensing both oxygen and $CO_2$ has been developed, which uses separate layers containing different dye-polymers for sensing different analytes, these sensors can also be difficult to manufacture, and may cause cross-interference in one or more of the indicator layers. There therefore remains a need for an optical fiber sensor including multiple dye indicators in a single matrix layer, for sensing multiple analytes.

While many optical fiber based sensor elements have been developed, there are also inherent problems commonly associated with them that are detrimental to the accuracy of the measurements. For example, it is sometimes difficult to immobilize the fluorescent dye in a gas permeable matrix because of a chemical incompatibility between the dye and matrix. Many of the more widely used fluorescent dyes are polynuclear aromatic compounds which have low solubility in organic materials. As a result, the fluorescent dyes have a tendency to leach through the permeable matrix into the solution or gas mixture that is being tested.

Various approaches for creating an operable sensor element include absorbing the dye on inorganic or organic solid supports, dispersing the dye in the matrix by way of organic solvents, and covalently bonding the dye on porous glass. Many of these techniques still have serious drawbacks if the dye is chemically incompatible with the polymer matrix. Such dyes can have a tendency to leach out, particularly when in contact with a sample that includes a substance that has similar properties as the dye polymer matrix. Unfortunately, such substances include blood proteins and many organic solvents, which are often present in the samples being tested. As a result of the leaching of the dye during use, the sensing element may have to be continuously replaced to ensure the accuracy of analyte measurements. Moreover, dye molecules that are free to move within a polymer matrix may also tend to agglomerate, which results in changes in their fluorescent properties.

One approach to construction of an optical sensor has involved the application of sensing material directly to the tip of the optical fiber, or the attachment of a dye filled porous glass to the tip of the optical fiber, by an adhesive. Another approach has involved the attachment of a sleeve which contains the dye indicator sensing material immobilized in a hydrophilic polymeric matrix, such as by entrapment in the matrix or by ionic interactions with the matrix, over the tip of the optical fiber. However, such sensors tend to eventually allow the indicator dye to leach out over extended time periods. Such leaching of the indicator dye results in increasingly inaccurate blood pH measurements.

Covalently bonding a dye indicator to an optical fiber core or to a polymer matrix secured over the core can reduce indicator leaching in such optical fiber sensors. In one approach, for example, the dye can be covalently bonded to the polymer, and the cross-linked polymer can in turn be covalently attached to the fiber. However, the dye loading of the carrier polymer is controlled by the fixed number of sites on the carrier polymer, and commonly only one type of functional group is available for dye attachment and crosslinking, even where the carrier polymer includes multiple dye bonding sites spaced to avoid physical cross-interference.

There thus remains a need for an optical fiber sensor which provides covalent linkages between the dye and matrix, and between the matrix and the optical fiber, to prevent leaching of the indicator material during periods of extended use of the sensor. It would also be desirable to provide such a dye matrix system to be formed from a copolymer to control not only the concentration of dye in the final sensor matrix, but also to control the relative proportions of different dyes in the final matrix. It would be desirable to provide such a copolymer system with different types of functional sites for bonding different dye indicators, and for crosslinking, which would allow the number of sites present on the carrier polymer to be altered depending upon the sensor requirements.

SUMMARY OF THE INVENTION

Briefly and in general terms, the present invention provides a new and improved optical fiber microsensor which includes one or more dye indicator materials covalently bonded to a copolymer, which is in turn covalently bonded with a crosslinking agent to the surface of the core of the optical fiber to prevent leaching of the indicator dye material during extended use. The dye-copolymer is crosslinked in situ over the tip of the optical fiber to yield an ion permeable sensor which can be used intravascularly to monitor one or more blood parameters.

The invention provides for a copolymer which is prepared to provide control of both the number of attachment sites available for indicator bonding and the number of crosslinking sites accessible during polymer curing. After dye attachment the copolymer is preferably crosslinked using a blocked isocyanato-polyether having a selectable number of crosslinking sites as the crosslinking agent. Thus both the relative proportions of multiple indicators and the crosslinking behavior can be closely controlled. Because the dye material is attached to a stable polymer which is completely miscible with the crosslinking component, the exact concentration of the dye indicators in the final sensor material can be quantified and closely controlled. The use of a blocked crosslinking agent also increases the ease of manufacturing the improved microsensor of the invention by prolonging pot life and allowing for on demand heat curing. A primer compound may be advantageously applied to a portion of the surface of the sensor member to provide sites for covalent bonding of the polymeric matrix, prior to covalently bonding the analyte sensing polymeric matrix to the surface of the sensor, to provide improved mechanical strength of the bonding between the matrix and the bonding surface.

These and other aspects and advantages of the invention will become apparent from the following detailed description and the accompanying drawings, which illustrate, by way of example, the features of the invention.

DETAILED DESCRIPTION OF THE PREFERRED EMBODIMENT

Problems of inaccuracies of analyte measurements have been found to result from the leaching of dye indicator materials during extended periods of use of the sensors, particularly in intravascular monitoring of blood analytes. In cases where a dye has been covalently bonded to a polymer which is in turn crosslinked and covalently attached to the fiber, dye loading in the polymer is controlled by the fixed number of sites on the carrier polymer, with only one type of functional group being available for both dye attachment and crosslinking of the polymer matrix.

In the current invention the number of sites on the carrier polymer for bonding of the dye material can be altered depending upon the sensor requirements. The current invention also provides a method of endowing the carrier polymer with a known percentage of functional sites for dye indicator bonding which are different from the functional sites for crosslinking of the polymer. This allows formulation of a custom polymer to which known amounts of one or more indicators can be attached, while still providing unique sites for crosslinking. When the crosslinking agent used is a blocked isocyanato-polyether and the carrier polymer's crosslinking group is chosen to be reactive with isocyanates the invention imparts long potlife to the prepolymer mixture, and allows rapid thermal cure of the sensor polymers.

According to the present invention, an optical fiber microsensor is prepared by covalently bonding the dye indicator material to a copolymer which permits control of both the number of attachment sites available for indicator bonding and the number of sites accessible to the crosslinking agent during polymer curing. After dye attachment the dye-copolymer is mixed with a blocked crosslinking agent, such as isocyanato-polyether, which is thereafter preferably simultaneously crosslinked and covalently bonded to the tip of the optical fiber. Thus both the indicator concentration and crosslinking behavior are controlled, and the use of the blocking agents has the advantage of extending the potlife of the copolymer. The use of blocking agents in preparing the final crosslinked copolymer also allows for on demand thermal curing of the dye matrix of the microsensor of the invention.

Figure 1:
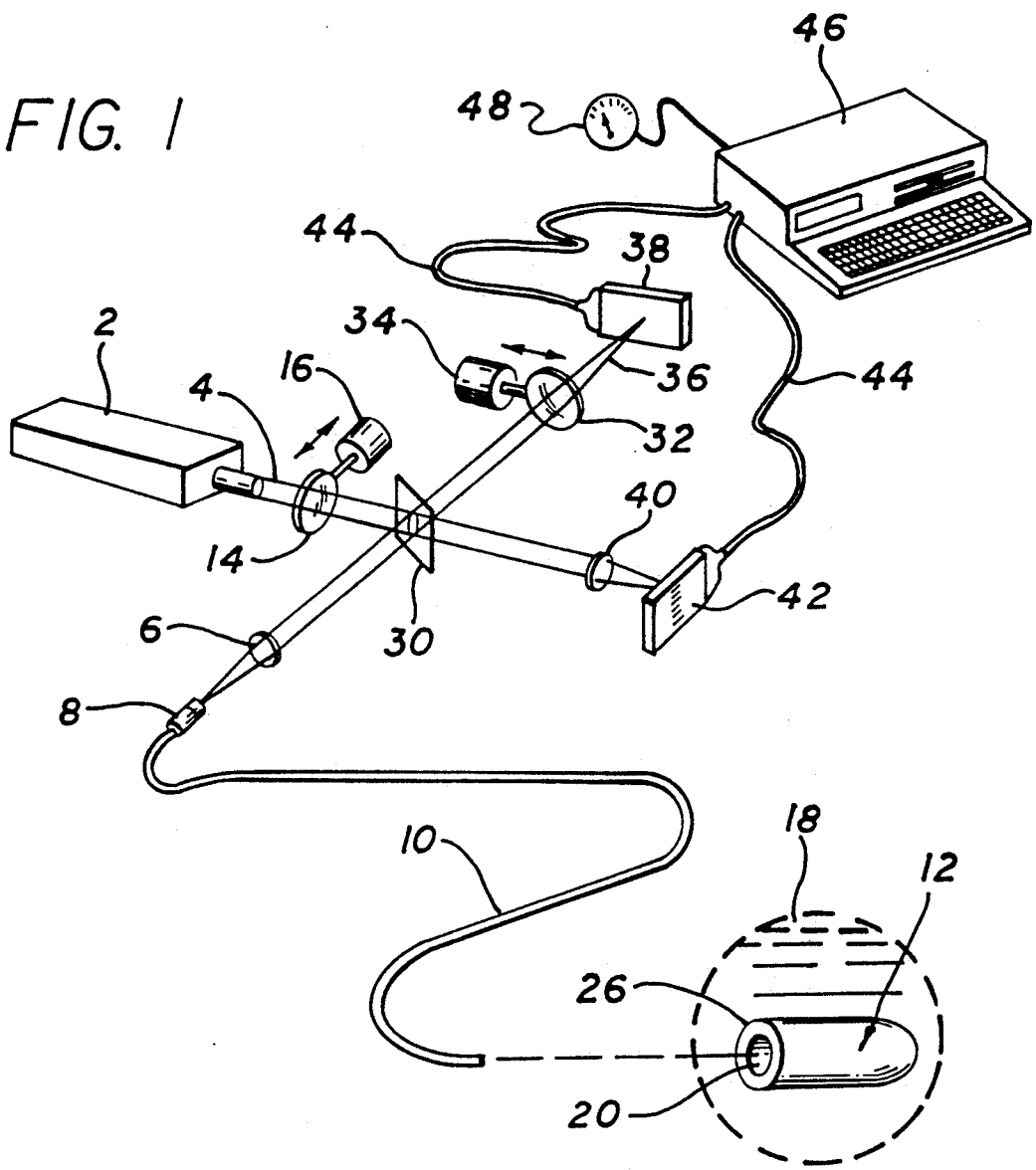
FIG. 1 is a perspective diagram of an optical fiber microsensor system utilizing the microsensor of the invention for monitoring blood parameters.

As is shown in the drawings, which are provided for purposes of illustration, the invention is embodied in an optical fiber microsensor which may be used for intravascular monitoring one or more blood parameters, and a method for making the microsensor. As is illustrated in FIG. 1, in such a system a light source 2 provides an output light beam 4 that is passed through a dichroic mirror 30 and focused by a lens system 6 into a connector 8 of an optical fiber 10, which carries the light beam to a sensor module 12 at a distal end of the optical fiber. The optical path preferably includes one or more excitation filters 14, actuated and controlled by stepper motor 16, for controlling the wavelength ranges of the light provided to the sensor module. Sensor module 12 is adapted to be placed in a fluid 18, such as blood, for quantitative measurement of a chemical parameter of the fluid, such as pH, or the partial pressures of carbon dioxide or oxygen. The sensor could, of course, be adapted to detect concentrations of analytes such as drugs, or other blood constituents.

Figure 2:
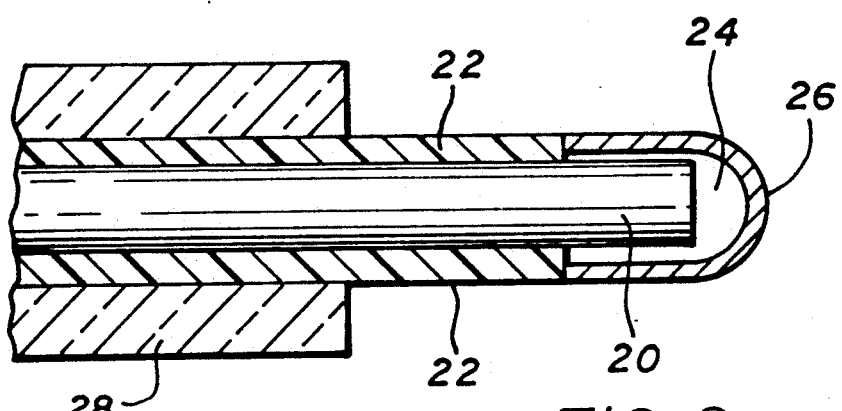
FIG. 2 is an enlarged, cross-sectional schematic diagram of the optical fiber microsensor.

As is illustrated in FIG. 2, the optical fiber sensor module is generally formed from an optical fiber having a light conducting core 20, such as glass, and an outer cladding material 22 having a refractive index such that light conducted by the core is substantially retained in the core material. A length of cladding on the distal end of the optical fiber is removed, leaving an exposed distal tip of the core. The exposed distal tip, preferably primed to provide sites for covalent attachment of a polymeric matrix, is coated with the polymeric matrix 24, which is preferably a mixture including the copolymer of the invention covalently bonded to one or more indicator dyes which are known to fluoresce in response to irradiation with light of one or more specific wavelength ranges.

The polymeric matrix is preferably formed from a mixture of a crosslinking agent which is a blocked form of a polyether polyisocyanate having a selected number of functional sites for crosslinking, such as that sold under the trademark "HYPOL" and made by W. R. Grace & Co., and a copolymer of hydroxyethyl methamethacrylate (HEMA) and aziridynyl ethyl methacrylate (AEMA) having a selected number of sites available for covalent bonding in a polyether polyamine form to one or more dye indicators, such as HPTS, and for covalent bonding with the crosslinking agent.

A coat of reflective material 26 is also preferably provided over the dye containing sensing matrix, to retain and reflect both the irradiating light and the fluorescence emissions from the dye indicator. The reflective coating is preferably a mixture containing titanium dioxide in a polyether polyisocyanate. The coating serves to provide protection, optical isolation and reflection of both the excitation and fluorescence emission light. In certain applications, an exterior coating or sheath 28 may be used to further facilitate or protect the optical fiber assembly.

The output optical fiber 10 may also carry light fluoresced from the dye indicators via a dichroic mirror 30 to emission filters 32 which may be actuated by stepper motor 34 and the fluorescent light beam 36 upon a detector array 38. Similarly, the portion of the light beam 4 that passes through the dichroic mirror 30 may be focused by a suitable lens 40 upon a reference detector array 42, which allows measurement of the excitation signal strength. The electrical output of the detectors is fed through cables 44 to a computer 46, such as an IBM PC, which receives the electrical output of the detectors and determines the blood analyte being monitored, such as pH. The computer is preferably programmed to measure the blood analyte based upon the specific measurement of fluorescence intensity represented by the electrical output signal received by the computer, according to an algorithm based upon signal outputs from measurements from samples with known levels of the analyte. The output of the computer may be indicated on a meter 48 or another suitable readout device.

As is shown in equation (i) below, the method of making the optical fiber microsensor involves first copolymerizing hydroxyethyl methacrylate (HEMA) and aziridynyl ethyl Methacrylate (AEMA) in the ratio of 20:1 HEMA to AEMA. The HEMA is preferably first purified to remove ethylene glycol dimethacrylate (EDGMA) and methacrylic acid (MAA), and the AEMA is preferably first dried and filtered. The polymerization may, for example, be run at 65 degrees C. in dimethyl formamide (DMF) and $K_2S_2O_8$ for 20–40 minutes. The resulting HEMA/AEMA copolymer is purified to remove unreacted monomer and very small polymer chains.

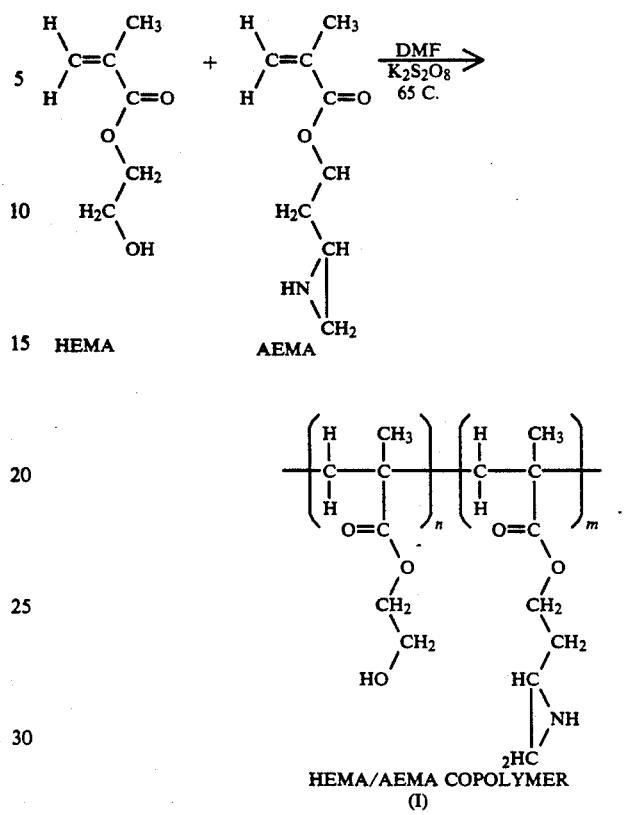

The dye indicator material, such as 8-hydroxy-1, 3, 6 pyrenetrisulfonic acid (HPTS) for example, is then attached to the HEMA/AEMA copolymer by first opening the aziridynyl ring using sodium carbonate followed by the addition of 8-acetoxy 1, 3, 6 pyrenetrisulfonyl chloride to covalently bond the dye to the HEMA/AEMA copolymer, forming HEMA/AEMA-HPTS, as shown in equation (II) below. Since the dye indicator material bonds to the aziridynyl portion of the AEMA monomer, the proportion of dye material in the resulting copolymer can be controlled according to the proportion of AEMA in the copolymer, and the proportion of aziridynyl sites open to bonding with other additional dye indicators, such as fluorescein, 7-hydroxycoumarins, seminaphthorhodafluor and seminaphthofluorescein, and with the crosslinking agent, can be closely controlled by the quantity and proportions of indicators dyes covalently bonded to the copolymer, as can be seen from Eq. IV. In addition, other dye indicators, such as fluorescein, 7-hydroxycoumarins, seminaphthorhodafluor and seminaphthofluorescein, may be bonded to the hydroxyl group of the HEMA portion of the copolymer, to form a multifunctional sensing matrix. The resulting HEMA/AEMA dye-copolymer is then preferably purified to remove unreacted dye materials.

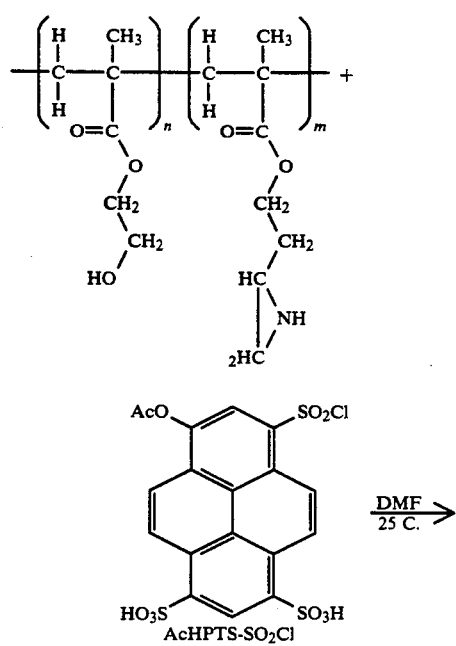 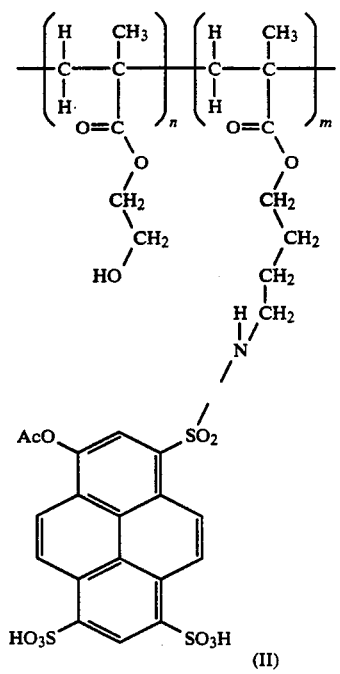

A blocked-isocyanate (BI-HYPOL) made from a polyether polyisocyanate having a desired number of isocyanate functional groups available for crosslinking, such as that sold under the trademark "HYPOL", can be prepared, for example, by dissolving a stoichiometric quantity of acetone oxime in an appropriate solvent such as acetone, adding a stoichiometric equivalent of the polyisocyanate in the form of the "HYPOL" prepolymer, and heating at 37 degrees C. overnight, as shown in equation III below:

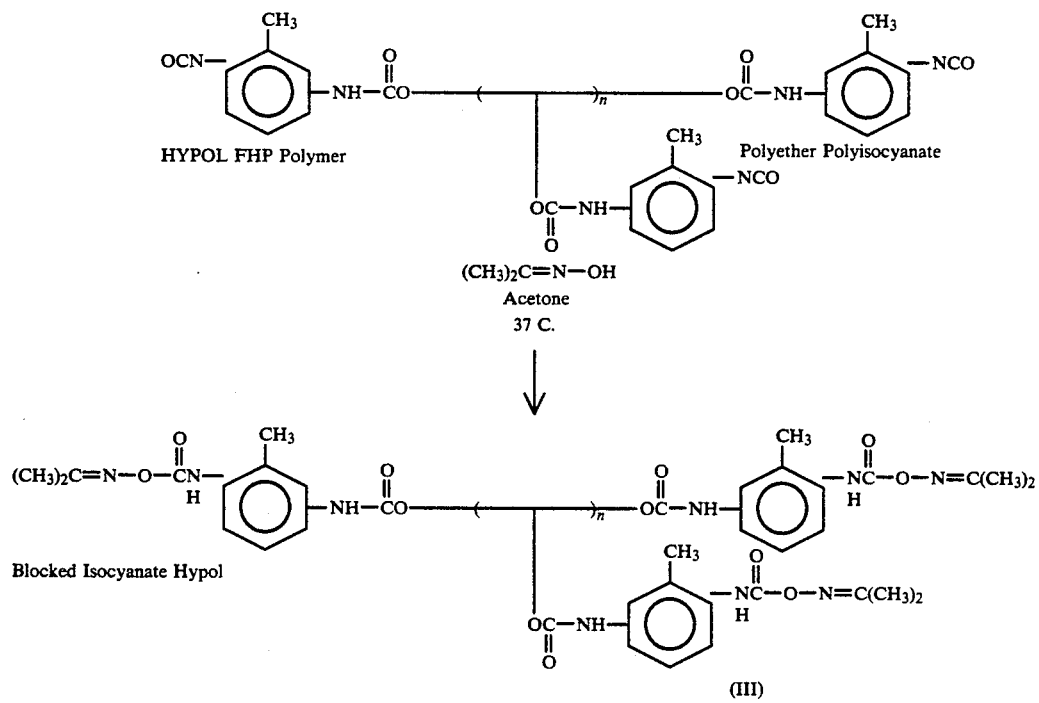

The HEMA/AEMA-HPTS dye-copolymer and a mixture of 37% BI-HYPOL in acetone are then mixed in a ratio of 2:1 of HEMA/AEMA-HPTS to BI-HYPOL. A 200 microliter aliquot of this mixture is removed and 20 microliters of water are added.
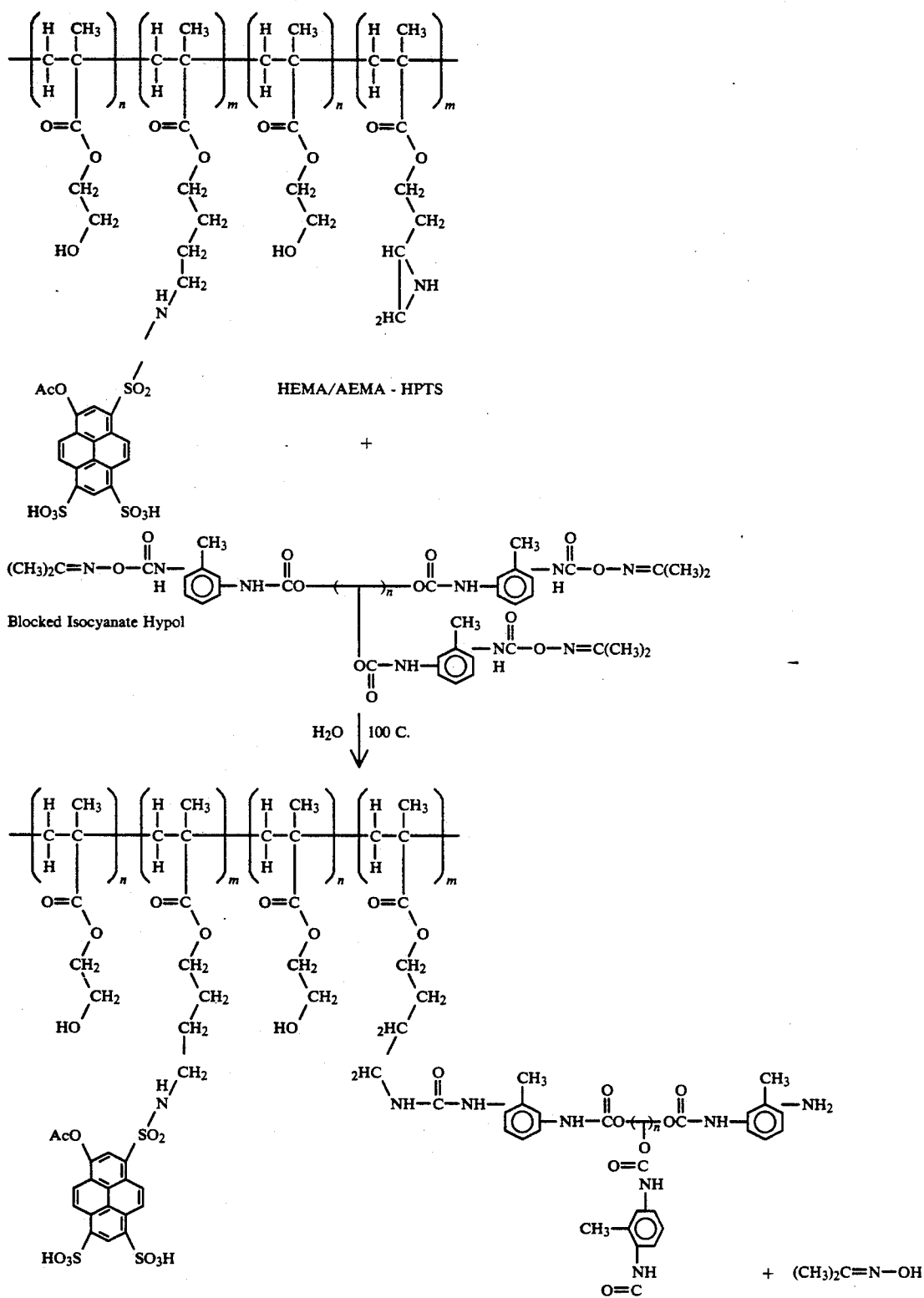

CROSSLINKED HEMA/AEMA-HPTS - HYPOL

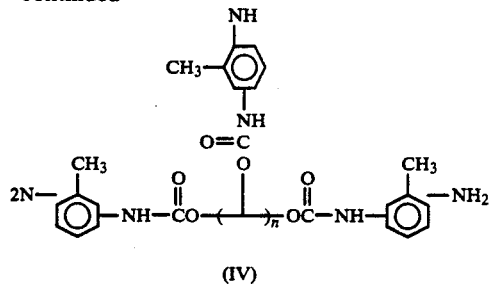

(IV)

This HEMA/AEMA-HPTS/BI-HYPOL prepolymer mixture is relatively stable and can be stored and applied in this form, and is easily characterizable. The concentration of the dye present in the polymer can be closely controlled, facilitating uniform application of the sensor material over a wide range of thicknesses of the sensor. The dye-copolymer mixture can be applied to the tips of glass fiber optic cable which have first been acid washed and then treated with a primer such as isocyanate propyltriethoxysilane. This provides a covalent attachment site for the polymer when it crosslinks and cures. The dye-indicator matrix can then be cured in situ, covalently bonding the matrix to the optical fiber, by heating the matrix to greater than 80 degrees C. for approximately 10 minutes. After the sensing matrix is completely solidified, a coating of reflective material 26, such as titanium dioxide in a polyether polyisocyanate or other such polymeric matrix, can be applied over the sensing matrix to optically isolate and protect the sensing matrix.

From the foregoing it will be appreciated that the invention provides an improved optical fiber microsensor which will prevent the problems of leaching of dye indicator materials during extended periods of intravascular monitoring of blood analyte levels, such as pH, oxygen, or carbon dioxide. It is significant that the optical fiber microsensor is prepared by covalently bonding the dye material to unique functional sites on the copolymer, and by covalently bonding the dye-copolymer to the tip of the optical fiber with a blocked crosslinking agent. As will be readily appreciated, the principles of the invention are applicable to other types of optical fiber microsensors such as blood oxygen and carbon dioxide sensors, in which similar problems of inaccuracies of analyte measurements have resulted from the leaching of dye indicator materials during extended periods of use of the sensors, particularly in intravascular monitoring of blood analytes.

While particular forms of invention have been illustrated and described, it will be apparent that various modifications can be made without departing from the spirit and scope of this invention. Accordingly, it is not intended that the invention be limited, except as by the appended claims.

What is claimed is:

1. An analyte sensor, comprising:
   an optical fiber having an outer bonding surface;
   an analyte sensing matrix covalently bonded to said bonding surface, the analyte sensing matrix including a copolymer having first and second monomer portions formed from a first monomer having a first type of functional group providing a bonding site for covalent bonding to a first dye indicator material, and a second monomer having a second type of functional group providing a bonding site for covalent bonding to a second dye indicator material and for cross-linking, said first and second monomer portions being provided in a ratio selected to control bonding of said second dye material and crosslinking;
   a first dye indicator material covalently bonded to said first monomer portion of said copolymer;
   a second dye indicator material covalently bonded to a portion of the bonding sites of said second monomer portion of said copolymer; and
   a crosslinking agent covalently bonded to said bonding surface and covalently bonded to a remaining portion of the bonding sites of said second monomer portion of said copolymer, whereby the proportion of bonding sites on said second monomer portion for crosslinking varies inversely with the proportion of said bonding sites of said second monomer portion covalently bonded to said second dye indicator material.

2. The sensor of claim 1, wherein said second monomer consists essentially of aziridynyl ethyl methacrylate.

3. The sensor of claim 2, wherein said first monomer consists essentially of hydroxyethyl methacrylate.

4. The sensor of claim 3, wherein said crosslinking agent consists essentially of a polyether isocyanate.

5. The sensor of claim 1, further including a coating of reflective material applied over the analyte sensing matrix.

6. The sensor of claim 1, wherein at least one of said first and second dye indicator materials comprises a fluorescent dye indicator.

7. The sensor of claim 1, wherein said first and second dye indicator materials comprise a plurality of different fluorescent dye indicator substances.

8. The sensor of claim 1, wherein said second dye indicator material comprises hydroxypyrenetrisulfonic acid.

9. A microsensor for measuring an analyte in a fluid, comprising:
   an optical fiber having a glass surface portion; an analyte sensing matrix formed from a copolymer of hydroxyethyl methacrylate monomer and aziridynyl ethyl methacrylate monomer;
   a first dye indicator material covalently bonded to said hydroxyethyl methacrylate monomer, and a second dye indicator material covalently bonded to said aziridynyl ethyl methacrylate monomer; and
   a polyether polyisocyanate crosslinking agent covalently bonded to the aziridynyl ethyl methacrylate monomer of said copolymer and to said glass surface portion.

10. The microsensor of claim 9, wherein said glass surface portion of said optical fiber has proximal and distal end portions with a light conducting inner core at the distal end portion of the optical fiber.

11. The sensor of claim 9, wherein at least one of said firs and second dye indicator materials is a fluorescent dye indicator.

12. The sensor of claim 9, wherein said first dye indicator material is selected from the group of dye indicator materials consisting of hydroxypyrenetrisulfonic acid, fluorescein, 7-hydroxycoumarins, seminaphthorhodafluor and seminaphthofluorescein, and said second dye indicator material is a different dye indicator material selected from said group.

13. A method of making an analyte sensor having an optical fiber with an outer bonding surface and an analyte sensing polymeric matrix covalently bonded to said bonding surface and including first and second covalently bonded dye indicator materials, comprising the steps of:
  forming a copolymer from first and second monomers, with said first monomer having a first type of functional group available as bonding sites for said first dye indicator material, and said second monomer having a second type of functional group available as bonding sites for said second dye indicator material and for crosslinking, said first and second monomers being provided in a ratio selected to control bonding of said second dye material and crosslinking;
  covalently bonding said first dye indicator material to said first type of functional group of said first monomer of said copolymer, and covalently bonding said second dye indicator material to a portion of the bonding sites of said second type of functional group of said second monomer to form a dye copolymer;
  mixing said dye copolymer with a crosslinking agent; and
  covalently bonding said crosslinking agent to said bonding surface and to at least a portion of remaining bonding sites of said second functional group of said second monomer of said dye copolymer to bond said analyte sensing polymeric matrix to said bonding surface, whereby the proportion of bonding sites on said second monomer available for crosslinking varies inversely with the proportion of said bonding sites on said second monomer covalently bonded to said second dye indicator material.

14. The method of claim 13, wherein said first monomer consists essentially of hydroxyethyl methacrylate and said second monomer consists essentially or aziridynyl ethyl methacrylate.

15. The method of claim 13, wherein said crosslinking agent consists essentially of a blocked polyether polyisocyanate.

16. The method of claim 15, wherein said bonding surface comprises an exposed surface of a glass light conducting core of said optical fiber, and said mixture of dye copolymer and polyether polyisocyanate is applied to a portion of the exposed surface of the glass light conducting core.

17. The method of claim 13, wherein the step of covalently bonding the crosslinking agent to said bonding surface comprises the steps of applying a primer compound to a portion of the outer surface of the optical fiber to provide sites for covalent bonding of the polymeric matrix, and covalently bonding said analyte sensing polymeric matrix to said primer compound to covalently bond said analyte sensing polymeric matrix to said outer bonding surface of said optical fiber.

18. The method of claim 13, wherein said first and second dye indicator materials comprise different dye indicator substances.

19. A method of making a microsensor for measuring an analyte in a fluid, said microsensor having an optical fiber having a glass surface portion, and a polymeric analyte sensing matrix covalently bonded to said glass surface portion, the polymeric analyte sensing matrix including a dye indicator material, comprising the steps of:
  covalently bonding a first dye indicator material to a copolymer of hydroxyethyl methacrylate and a second dye indicator material to aziridynyl ethyl methacrylate having bonding sites for bonding to said second dye indicator material and for crosslinking to form a dye copolymer;
  forming a blocked polyether isocyanate by reacting stoichiometric equivalent quantities of acetone oxime and a polyether polyisocyanate;
  mixing water with said dye copolymer and said blocked polyether polyisocyanate to initiate crosslinking between said dye copolymer and said blocked polyether polyisocyanate to form said polymeric analyte sensing matrix;
  applying said polymeric analyte sensing matrix in which crosslinking has been initiated to said glass surface portion of said optical fiber; and
  heating said polymeric analyte sensing matrix on said glass surface portion of said optical fiber to a temperature greater than 80 degrees Celsius for a sufficient time to cure said polymeric analyte sensing matrix and to form a covalent bond between said polymeric analyte sensing matrix and said glass surface portion of said optical fiber.

20. The method of claim 19, wherein said glass surface portion comprises an exposed surface of a glass light conducting core of said optical fiber, and said mixture of dye copolymer and said blocked polyether polyisocyanate in which crosslinking has been initiated is applied to a portion of the exposed surface of the glass light conducting inner core.

21. The method of claim 19, wherein said first dye indicator material is selected from the group of dye indicators consisting of hydroxypyrenetrisulfonic acid, fluorescein, 7-hydroxycoumarins, seminaphthorhodafluor and seminaphthofluorescein, and said second dye indicator material is a different dye indicator selected from said group.

22. The method of claim 19, further including the step of applying a primer compound to the glass surface portion of the optical fiber to provide sites for covalent bonding of the polymeric matrix, prior to the step of applying said polymeric analyte sensing matrix in which crosslinking has been initiated to said glass surface portion of said optical fiber.

23. The method of claim 19, wherein said first and second dye indicator materials are different, and further comprising the step of providing said hydroxyethyl methacrylate and said aziridynyl ethyl methacrylate in a ratio selected to control the proportion of sites on said dye copolymer for covalent bonding of said dye indicator material to said copolymer and providing said second dye indicator material and said blocked polyether isocyanate in a ratio selected to control the proportion of sites on said polyether polyisocyanate for crosslinking said dye copolymer and said blocked polyether polyisocyanate.

* * * * *